Figure 1:
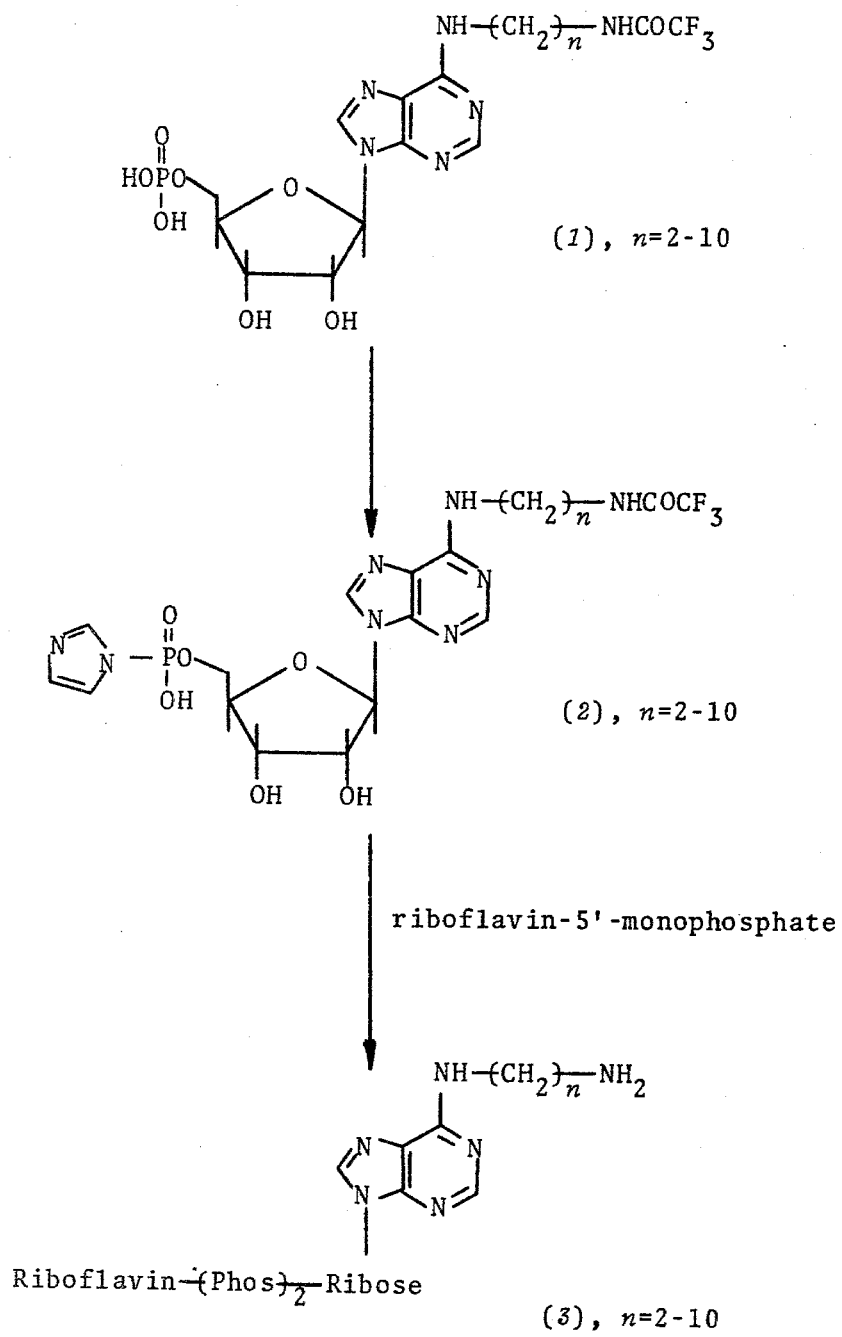

United States Patent [19]

Carrico et al.

[11] 4,255,566
[45] Mar. 10, 1981

[54] FLAVIN ADENINE DINUCLEOTIDE DERIVATIVES AND LABELED CONJUGATES PREPARED THEREFROM

[75] Inventors: Robert J. Carrico; Richard D. Johnson, both of Elkhart, Ind.

[73] Assignee: Miles Laboratories, Elkhart, Ind.

[21] Appl. No.: 122,292

[22] Filed: Feb. 19, 1980

[51] Int. Cl.³ .................. C07H 19/20; C07H 17/00
[52] U.S. Cl. .................................. 536/27; 536/28; 536/29
[58] Field of Search .................. 536/26, 27, 28, 29

[56] References Cited

U.S. PATENT DOCUMENTS 4,171,432  10/1979  Carrico et al. .................. 536/26

Primary Examiner—Johnnie R. Brown
Assistant Examiner—Blondel Hazel
Attorney, Agent, or Firm—Andrew L. Klawitter

[57] ABSTRACT

A flavin adenine dinucleotide (FAD) derivative of the formula:

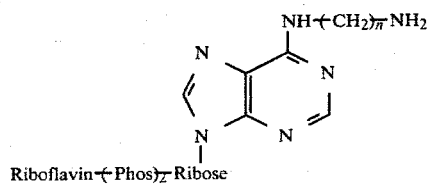

wherein n is an integer from 2 through 10, and preferably is 6. The derivatives are intermediates in the preparation of FAD-labeled conjugates useful as reagents in specific binding assays for determining ligands (e.g., antigens and haptens) in liquid media such as serum. Also provided are certain FAD-labeled conjugates, particularly an FAD-theophylline conjugate.

10 Claims, 4 Drawing Figures

FLAVIN ADENINE DINUCLEOTIDE DERIVATIVES AND LABELED CONJUGATES PREPARED THEREFROM

BACKGROUND OF THE INVENTION

1. Field of the Invention

This invention relates to certain derivatives of flavin adenine dinucleotide (FAD) which are useful as intermediates in the synthesis of FAD-labeled conjugates used as reagents in specific binding assays.

Flavin adenine dinucleotide has the following chemical structure [*The Merck Index*, 9th ed. (1976) p. 532]:

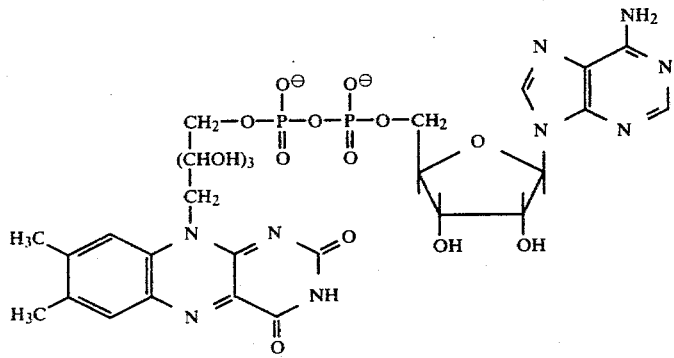

which hereinafter is abbreviated as:

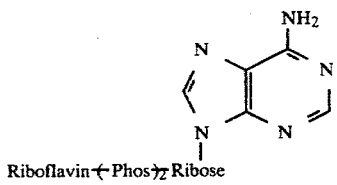

wherein Riboflavin-(-Phos-)$_2$Ribose represents the riboflavin-pyrophosphate-ribose residue in FAD.

2. Description of the Prior Art

Specific binding assay methods have undergone a technological evolution from the original competitive binding radioimmunoassay (RIA) in which a radioisotope-labeled antigen is made to compete with antigen from a test sample for binding to specific antibody. In the RIA technique, sample antigen is quantitated by measuring the proportion of radioactivity which becomes associated with the antibody by binding of the radiolabeled antigen (the bound-species of the labeled antigen) to the radioactivity that remains unassociated from antibody (the free-species) and then comparing that proportion to a standard curve. A comprehensive review of the RIA technique is provided by Skelly et al, *Clin. Chem.* 19:146(1973). While by definition RIA is based on the binding of specific antibody with an antigen or hapten, radiolabeled binding assays have been developed based on other specific binding interactions, such as between hormones and their binding proteins. All radiolabeled specific binding assays are by necessity heterogeneous, that is, the bound- and free-species of the labeled conjugate must be physically separated and the label (i.e., radioactivity) measured in one of the separated species.

From the radiolabeled binding assays have evolved nonradioisotopic binding assays employing labeling substances such as enzymes as described in U.S. Pat. Nos. 3,654,090 and 3,817,837. Recently, further improved nonradioisotopic binding assays have been developed as described in German Offenlegungschriften Nos. 2,618,419 and 2,618,511, based on U.S. Ser. Nos. 667,982 and 667,996, filed on Mar. 18, 1976 and assigned to the present assignee, employing particularly unique labeling substances, including coenzymes, cyclic reactants, cleavable enzyme substrates, and chemiluminescent molecules. Flavin adenine dinucleotide (FAD) is mentioned as being useful as a coenzyme label since FAD functions as a coenzyme in reactions which can be used to monitor specific binding reactions. The majority of the recently developed nonradioisotopic specific binding assays can be performed in a homogeneous format, that is, without separating the bound- and free-species of the labeled conjugate, due to the fact that the label expresses a different activity in the bound-species compared to the free-species. In particular, FAD has been found to be useful as a prosthetic group label as described in U.S. patent applications Ser. Nos. 917,961 and 45,423, filed June 22, 1978 and June 4, 1979, respectively, both assigned to the present assignee. U.S. Pat. No. 4,171,432 issued to the present assignee and U.S. patent application Ser. No. 950,858, filed Oct. 12, 1978 and assigned to the present assignee, describe certain FAD-labeled conjugates and intermediates in the synthesis thereof.

Modification of FAD and related adenine derivatives is described in *Eur. J. Biochem* 89:491(1978) and U.S. Pat. No. 4,008,363.

SUMMARY OF THE INVENTION

The novel FAD derivatives provided by the present invention are the flavin $N^6$-($\omega$-aminoalkyl)-adenine dinucleotides of the formula:

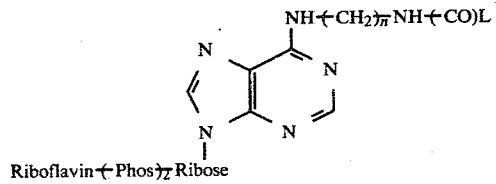

wherein, as stated above, Riboflavin-(-Phos-)$_2$Ribose represents the riboflavin-pyrophosphate-ribose residue in FAD and wherein n is an integer from 2 through 10, preferably 6. The FAD derivatives are used as intermediates in the synthesis of FAD-labeled conjugates used in binding assays for determining ligands, or binding partners thereof, of analytical interest in liquid media such as serum. The FAD-labeled conjugates are particularly useful as reagents in the assay referred to hereinbefore which employs a prosthetic group label, and have the general formula:

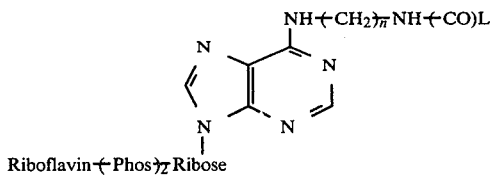

wherein n is as defined above and —(CO)L represents a specifically bindable ligand, or an analog thereof, bound through an amide bond.

The specifically bindable ligand or analog thereof in the present labeled conjugates, in terms of its chemical nature, usually is a protein, polypeptide, peptide, carbohydrate, glycoprotein, steroid, or other organic molecule for which a specific binding partner is obtainable. In functional terms, the ligand will usually be an antigen or an antibody thereto; a hapten or an antibody thereto; or a hormone, vitamin, or drug, or a receptor or binding substance therefor. Most commonly, the ligand is an immunologically-active polypeptide or protein of molecular weight between 1,000 and 4,000,000 such as an antigenic polypeptide or protein or an antibody; or is a hapten of molecular weight between 100 and 1,500.

As is more fully described in the Examples below, the present flavin $N^6$-($\omega$-aminoalkyl)-adenine dinucleotides can be prepared as follows. 6-Chloro-$\beta$-D-ribofuransoylpurine is phosphorylated by treatment with phosphoryl chloride, yielding 6-chloropurine-5'-monophosphate, which upon reaction with $\alpha,\omega$-alkanediamines (having a linear alkyl chain of 2–10 carbons) produce $N^6$-($\omega$-aminoalkyl)-adenosine-5'-monophosphates [Trayer et al, Biochem. J. 139:609(1974)]. Continuing with the method of Trayer et al, the derivatized adenosine-5'-monophosphates are treated with ethyl trifluorothiolacetate to block the terminal $N^6$ amino group and with carbonyldiimidazole to block the phosphate group, yielding $N^6$-($\omega$-trifluoroacetamidoalkyl)-adenosine-5'-monophosphate imidazolides. Reaction with riboflavin monophosphate in the presence of dimethylformamide, followed by treatment with base, produces the desired $N^6$-($\omega$-aminoalkyl)-adenine dinucleotides.

The FAD-labeled conjugates are prepared by linkage, through formation of a peptide or amide couple, with either the ligand of analytical interest, where such contains a carboxylic acid function, or a binding analog of the ligand (e.g., a derivative of the ligand) which analog contains the desired carboxylic acid function. Such condensation reactions can be accomplished by reacting the $N^6$-aminoalkyl-FAD intermediate directly with the carboxylic acid-containing ligand or ligand analog using conventional peptide condensation reactions such as the carbodiimide reaction [Science 144:1344(1964], the mixed anhydride reaction [Erlanger et al, Methods in Immunology and Immunochemistry, ed. Williams and Chase, Academic Press (New York 1967) p. 149], and the acid azide and active ester reactions [Kopple, Peptides and Amino Acids, W. A. Benjamin, Inc. (New York 1966)]. See also for a general review Clin. Chem, 22:726(1976).

It will be recognized, of course, that other well known methods are available for coupling the ligand or a derivative thereof to the $N^6$-aminoalkyl-FAD intermediate. In particular, conventional bifunctional coupling agents can be employed for coupling a ligand, or its derivative, containing a carboxylic acid or amino group to the amino intermediate. For example, amine-amine coupling agents such as bis-isocyanates, bis-imidoesters, and glutaraldehyde [Immunochem. 6:53(1969)] can be used to couple a ligand or derivative containing an amino group to the amino intermediate. Also, appropriate coupling reactions are well known for inserting a bridging group in coupling an amine (e.g., the amino intermediate) to a carboxylic acid (e.g., the ligand or a derivative thereof). Coupling reactions of this type are thoroughly discussed in the literature, for instance in the above-mentioned Kopple monograph and in Lowe & Dean, Affinity Chromatography, John Wiley & Sons (New York 1974). Such coupling techniques will be considered equivalents to the previously discussed peptide condensation reactions in preparing useful labeled conjugates. The choice of coupling technique will depend on the functionalities available in the ligand or analog thereof for coupling to the amino intermediate and on the length of the bridging group desired.

The FAD-labeled conjugates are used in binding assays for the ligand or a specific binding partner therefor and are determined, i.e., monitored, for the purposes of the assay by measuring FAD activity, e.g., the coenzyme or prosthetic group activity of the labeled conjugate. Preferably the FAD-labeled conjugates are monitored by measuring holoenzyme activity generated upon combination of such conjugate with an apoenzyme that requires FAD to perform its catalytic function as described in detail in the above-mentioned U.S. patent applications Ser. Nos. 917,961 and 45,423.

The present invention will now be illustrated, but is not intended to be limited, by the following Examples.

EXAMPLE 1

Preparation of $N^6$-$\omega$-aminoalkyl derivatives of flavin adenine dinucleotide The general reaction sequence for preparing the FAD-derivatives according to the present invention is shown in FIG. 1 of the drawings. This sequence is exemplified below for preparing flavin $N^6$-(6-aminohexyl)-adenine dinucleotide (3, n=6).

$N^6$-Trifluoroacetamidohexyl-adenosine-5'-monophosphate (1, n=6) was synthesized by reacting 6-chloropurineriboside-5'-monophosphate with 1,6-hexanediamine according to the method of Trayer et al, Biochem. J. 139:609(1974), followed by blocking the terminal amino group with trifluoroacetyl.

Fifty-six milligrams (mg) [0.1 millimole (mmol)] of $N^6$-trifluoroacetamidohexyl-adenosine-5'-monophosphate (1, n=6) was dissolved in about 10 milliliters (ml) of water and 25 microliters ($\mu$l) of tri-n-butylamine (0.1 mmol) was added. The water was removed under vacuum and the residue was dissolved in 10 ml of dry dimethyl formamide (DMF) which was then removed under vacuum. The residue was evaporated from dry DMF three more times. The final residue was dissolved in 10 ml of dry DMF. Eighty milligrams of N,N'-carbonyldiimidazole (0.4 mmol) was added and allowed to react for 1.5 hours. Then 15 $\mu$l of water was added and the solvent was removed under vacuum. The residue [$N^6$-trifluoroacetamidohexyl-adenosine-5'-monophosphate imidazolide (2, n=6)] was dissolved in 10 ml of DMF.

Forty-seven milligrams of riboflavin-5'-monophosphate (0.1 mmol), prepared as described by Johnson et al, *Anal. Biochem.* 86:526(1978), was dissolved in about 10 ml of water and added dropwise to 20 ml of acetone containing 43 μl of tri-n-octylamine (0.1 mmol). A precipitate formed before the addition was complete. The solvent was removed with a rotary evaporator until the riboflavin-5'-monophosphate dissolved. Then 5 ml of acetone and 5-10 ml of DMF were added and the mixture was taken to dryness. The residue was dissolved in 15-20 ml of dry DMF and taken to dryness (this process was repeated three times). The residue was dissolved in 5 ml of dry DMF and combined with the above-mentioned 10 ml solution of the imidazolide (2, n=6) in dry DMF.

The reaction mixture was allowed to stand at room temperature overnight and then the solvent was removed. The residue was taken up in 50 ml of water and applied to a 2.5×25 centimeter (cm) column of DEAE-cellulose in the bicarbonate form (Whatman DE23, Reeve Angel, Clifton, N.J.). The chromatogram was developed with a linear gradient generated with two liters of water and two liters of 0.3 molar (M) ammonium bicarbonate (23 ml fractions were collected). Thin-layer chromatography on silica gel 60 F254 (E. Merck, Darmstadt, West Germany) using a 7:3 volume:volume (v:v) mixture of ethanol—1 M triethylammonium bicarbonate (pH 7.5) showed that fractions numbered 68 to 73 contained major ($R_f$=0.75) and minor ($R_f$=0.36) yellow components. These fractions were pooled and the optical absorption spectrum had maxima at 267, 373 and 450 nanometers (nm).

The solvent was removed from the pooled material and the residue was dissolved in about 5 ml of water. This solution was adjusted to pH 11.0 with 5 N sodium hydroxide and allowed to stand at room temperature for nine hours. Thin-layer chromatography showed that the component with $R_f$=0.75 disappeared while a new yellow material with $R_f$=0.37 appeared. The latter material gave a positive reaction with ninhydrin. Some yellow material with $R_f$=0.75 was not changed by the alkaline conditions and was probably riboflavin cyclic-4',5'-monophosphate.

The reaction mixture was adjusted to pH 8.0 with hydrochloric acid and applied to a 2.5×20 cm column of DEAE-cellulose in the bicarbonate form. The chromatogram was developed with a linear gradient developed with one liter of water and one liter of 0.2 M ammonium bicarbonate. Separation of the major yellow components was not achieved. The yellow effluent from the column was pooled and the solvent was removed. The residue was adsorbed onto 2 grams (g) of silica gel which was placed atop a 50 g column of silica gel equilibrated with a 9:2 (v:v) mixture of ethanol—1 M triethylammonium bicarbonate (pH 7.5). When the column was washed with this same solvent mixture, the yellow component with $R_f$=0.75 eluted with considerable tailing. The solvent ratio was changed to 8:2 and the yellow component with $R_f$=0.37 eluted along with some of the material with $R_f$=0.75. The yellow effluent containing the component with $R_f$=0.37 was collected and the solvent was removed. The yield of the FAD derivative (3, n=6) based on absorbance at 450 nm was about 10%.

This material had optical absorption maxima at 265, 373, and 450 nm. A sample was spotted on a thin-layer chromatography plate which was developed with ethanol—1 M triethylammonium bicarbonate, pH 7.5 (7:3). The yellow bands were scraped from the plate and the yellow compounds were each eluted from the silica gel with water. Absorbance measurements at 450 nm indicated that the components with $R_f$=0.37 and 0.75 represented 70% and 30% respectively, of the flavins in the mixture. A sample of the mixture was dissolved in 0.1 M tris-(hydroxymethyl)-aminomethane-hydrochloride buffer, pH 8.5, and allowed to react overnight with a snake venom phosphodiesterase preparation (*Croteus adamatous*) obtained from Worthington Biochemicals, Freehold, N.J. The material with $R_f$=0.37 was completely hydrolyzed to flavin mononucleotide (FMN) while the material with $R_f$=0.75 was not affected. In a control reaction, the snake venom preparation hydrolyzed FAD to FMN.

The above-described synthesis of the $N^6$-ω-aminoalkyl derivative of FAD (3, n=6) can be modified to yield derivatives wherein n=2-10 by replacing the starting material 1,6-hexanediamine with the appropriate α,ω-alkanediamine as follows:

| n | α,ω-alkanediamine |
|---|---|
| 2 | ethylenediamine |
| 3 | 1,3-propanediamine |
| 4 | 1,4-butanediamine |
| 5 | 1,5-pentanediamine |
| 7 | 1,7-heptanediamine |
| 8 | 1,8-octanediamine |
| 9 | 1,9-nonanediamine |
| 10 | 1,10-decanediamine |

EXAMPLE 2

Homogeneous Binding Assay for
N-2',4'-Dinitrophenyl-6-aminocaproate

I. Preparation of the labeled conjugate—flavin $N^6$-{6-[N-(2',4'-dinitrophenyl)]aminohexyl}adenine dinucleotide (DNP-FAD).

The residue from Example 1 containing flavin $N^6$-(6-aminohexyl)-adenine dinucleotide was purified by chromatography on Sephadex G-10 (Pharmacia Fine Chemicals, Uppsala, Sweden). To a 0.9×30 cm column equilibrated with 25 millimolar (mM) sodium bicarbonate (pH 7.5) at room temperature was applied 1 ml of an approximately 10 mM solution of the FAD derivative in water. The first eluted peak of material absorbing at 450 nm was collected and rechromatographed on Sephadex G-10 and the first eluting peak collected again.

One-half milliliter (0.63 μmol) of the purified FAD derivative in 25 mM sodium bicarbonate (pH 7.5) was mixed with 2 ml of ethanol and 10 μl of $^3$H-dinitrofluorobenzene (6.3 μmol, 50 μCi) in ethanol were added (the tritiated dinitrofluorobenzene was obtained from the Radiochemical Centre, Amersham, England). The reaction mixture was shaken continuously overnight in the dark at room temperature and then applied to a 0.9×30 cm column of Sephadex G-10 equilibrated with 0.1 M phosphate buffer (pH 7.0) containing 0.1% sodium azide. The single peak of material absorbing at 450 nm was collected and found to contain 8% of the radioactive label.

II. Preparation of apoglucose oxidase

Purified glucose oxidase with low catalase activity obtained from the Research Products Division of Miles Laboratories, Inc., Elkhart, Ind., was dialyzed twice for 12 hours each against 0.5% weight:volume (w:v) mannitol (30 volumes each). Aliquots of the dialysate containing 100 mg of glucose oxidase each were lyophilized and stored at −20° C.

Bovine serum albumin (200 mg) was dissolved in 12 ml of water adjusted to pH 1.6 with concentrated sulfuric acid, mixed with 150 mg charcoal (RIA grade from Schwarz-Mann, Orangeburg, N.Y.), and cooled to 0° C. Lyophilized glucose oxidase (100 mg) was redissolved in 3.1 ml of water and 3 ml was added to the stirred albumin-charcoal suspension with continued stirring for 3 minutes. The suspension was then filtered through a 0.8 micron, 25 millimeter (mm) diameter Millipore filter (Millipore Corp., Bedford, Mass.) mounted in a Sweenex filter apparatus (Millipore Corp.) on a 50 ml disposable plastic syringe. The filtrate was quickly neutralized to pH 7.0 by addition of 2 ml of 0.4 M phosphate buffer (pH 7.6) and thereafter 5 N sodium hydroxide. Dry charcoal (150 mg) was then added and stirred for one hour at 0° C. The resulting suspension was filtered first through a 0.8 micron Millipore filter and then through a 0.22 micron Millipore filter. To the filtrate was added glycerol to 25% (v:v) and the stabilized apoglucose oxidase preparation was stored at 4° C.

III. Assay Reagents

1. Labeled conjugate—DNP-FAD (from Part I) was diluted in 0.05 M phosphate buffer (pH 7.0) to a concentration of 118 nanomolar (nM).

2. Apoenzyme—Apoglucose oxidase (from Part II) was diluted with 0.1 M phosphate buffer (pH 7.0) containing 0.1% bovine serum albumin to a concentration of 958 nM FAD binding sites. The FAD binding site concentration of the apoenzyme preparation was determined experimentally by measuring the minimum amount of FAD required to give maximum glucose oxidase activity when incubated with the apoenzyme.

3. Antiserum—Antiserum against a dinitrophenyl-bovine serum albumin conjugate was obtained from Miles-Yeda, Ltd., Rehevot, Israel, and was diluted 31 fold in 0.1 M phosphate buffer (pH 7.0) containing 0.1% bovine serum albumin.

4. Standards—The standard solutions contained known concentrations of N-2',4'-dinitrophenyl-6-aminocaproate prepared in 0.05 M phosphate buffer (pH 7.0).

5. Monitoring reagent—A glucose oxidase reagent was prepared by mixing 45 ml of 0.1 M phosphate buffer (pH 7.0) containing 15 mM ethylenediamine tetraacetic acid, 9 ml of 11.5 mM 3,5-dichloro-2-hydroxybenzene sulfonate in water adjusted to pH 7 with sodium hydroxide, 9 ml of 11.5 mM 4-aminoantipyrine in water containing 1.25 mg/ml of peroxidase (Miles Laboratories, Inc., Elkhart, Ind.), and 6 ml of 1.0 M glucose in aqueous saturated benzoic acid solution.

IV. Assay Procedures

1. Addition of apoenzyme with initiation of binding reaction

Method #1—The following were added in sequence to separate reaction cuvettes: 0.1 ml of the labeled conjugate solution, 0.05 ml of a selected standard solution, 0.1 ml of the antiserum solution, 2.0 ml of the monitoring reagent, and 0.1 ml of the apoenzyme solution. Each reaction mixture was incubated for 30 minutes at 30° C. and the absorbance at 520 nm measured.

Method #2—The following were added in sequence to separate reaction cuvettes: 0.1 ml of the labeled conjugate solution, 0.05 ml of a selected standard solution, 0.1 ml of the antiserum solution, and 0.1 ml of the apoenzyme solution. Each reaction mixture was incubated for 20 minutes at room temperature and then 2.0 ml of the monitoring reagent was added to each. After further incubation for 15 minutes at 30° C. the absorbance at 520 nm was measured in each cuvette.

2. Addition of apoenzyme after initiation of binding reaction

Method #3—The following were added in sequence to separate reaction cuvettes: 0.1 ml of labeled conjugate solution, 0.05 ml of a selected standard solution, and 0.1 ml of the antiserum solution. Each reaction mixture was incubated for 20 minutes at room temperature and then 2.0 ml of the monitoring reagent and 0.1 ml of the apoenzyme solution were added to each. After further incubation for 30 minutes at 30° C. the absorbance at 520 nm was measured in each cuvette.

Method #4—The following were added in sequence to separate reaction cuvettes: 0.1 ml of the labeled conjugate solution, 0.05 ml of a selected standard solution, and 0.1 ml of the antiserum solution. Each reaction mixture was incubated for 20 minutes at room temperature and then 0.1 ml of the apoenzyme solution was added to each. After further incubation for 20 minutes 2.0 ml of the monitoring reagent was added to each cuvette. Then each reaction mixture was incubated for 15 minutes at 30° C. and the absorbance at 520 nm was measured in each cuvette.

V. Results

Following is Table 1 showing the results of the four assay procedures in measuring N-2',4'-dinitrophenyl-6-aminocaproate. The concentrations of N-2',4'-dinitrophenyl-6-aminocaproate are expressed as concentrations in the final 2.35 ml reaction mixture volumes. The absorbance results are expressed as the average of duplicate runs corrected for residual enzyme activity and background absorbance in the reagents. The correction factor is given for each assay method at the end of Table 1 and was determined by the experimental runs substituting 0.1 M phosphate buffer (pH 7.0) for each of the labeled conjugate, standard, and antiserum solutions.

TABLE 1

| Concentration of N-2', 4'-dinitrophenyl-6-aminocaproate (nM) | Corrected Average Absorbance at 520 nm | | | |
|---|---|---|---|---|
| | Method #1 | Method #2 | Method #3 | Method #4 |
| 1021 | 0.274 | 1.089 | 0.205 | 1.399 |
| 511 | 0.263 | 0.992 | 0.197 | 1.302 |
| 255 | 0.235 | 0.898 | 0.187 | 1.136 |
| 128 | 0.221 | 0.689 | 0.173 | 0.958 |
| 64 | 0.194 | 0.545 | 0.155 | 0.737 |
| 32 | 0.165 | 0.365 | 0.134 | 0.534 |
| 16 | 0.141 | 0.276 | 0.133 | 0.353 |
| 8 | 0.134 | 0.225 | 0.122 | 0.257 |
| 4 | 0.122 | 0.193 | 0.104 | 0.229 |
| 2 | 0.123 | 0.187 | 0.109 | 0.215 |
| 0 | 0.107 | 0.171 | 0.101 | 0.199 |
| * * * * * * * * * | | | | |
| correction factor | 0.241 | 0.108 | 0.216 | 0.108 |

EXAMPLE 3

Homogeneous Binding Assay For Theophylline

I. Preparation of the labeled conjugate-theophylline-FAD

Figure 2:
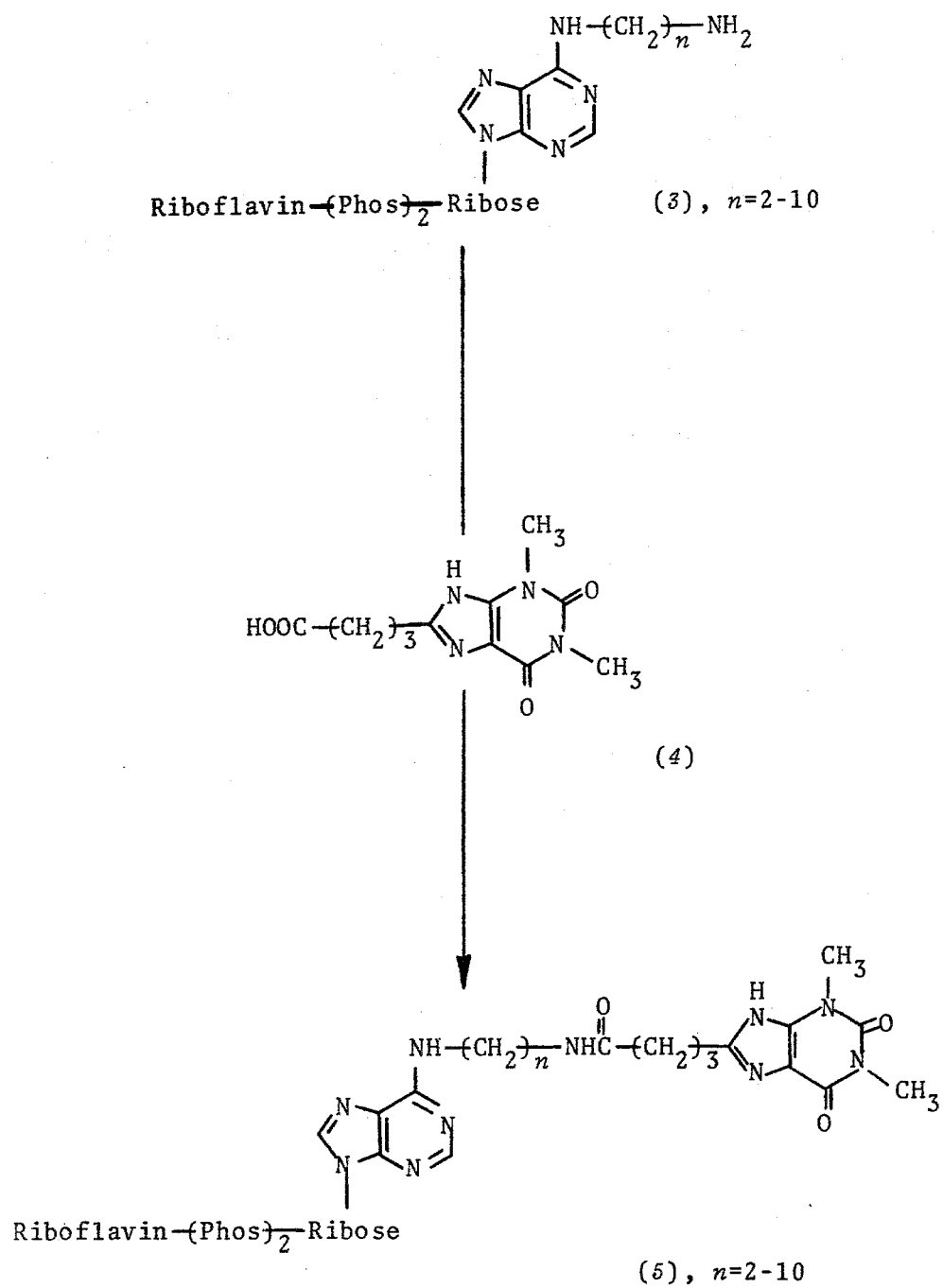

The general reaction sequence for preparing theophylline-FAD conjugates according to the present invention is shown in FIG. 2 of the drawings. This sequence is exemplified below wherein n=6.

To a solution of 2.4 μmol flavin $N^6$-(6-aminohexyl)-adenine dinucleotide (3, n=6) prepared as described in Example 1 above, in 200 μl dimethylsulfoxide under argon gas was added 0.9 mg (3.62 μmol) 1,3-dimethyl-1,6,7,8-tetrahydropyrido[1,2-e]purine-2,4,9(3H)-trione (4), prepared according to the method of Cook et al, *Res. Comm. in Chem. Pathol. and Pharm.* 13:497(1976), followed after 4 hours by addition of a further 1.8 mg (7.3 μmol) of the same (trione). After stirring overnight, the solvent was evaporated under vacuum (0.1 mm Hg) and the residue chromatographed on a 2.5×90 cm LH-20 Sephadex (Pharmacia Fine Chemicals, Uppsala, Sweden) column equilibrated and eluted with 0.3 M triethylammonium bicarbonate buffer (pH 7.8). The crude product eluting between 216 and 246 ml of the effluent was collected, applied to a 20×20 cm × 1000μ silica gel plate and chromatographed using an 8:2 ethanol: 1 M triethylammonium bicarbonate buffer (pH 7.8) mixture. The band containing the desired product ($R_f$=0.77) was scraped from the plate, extracted with 1 M triethylammonium bicarbonate buffer (pH 7.8), filtered and concentrated. Final purification by chromatography on LH-20 Sephadex equilibrated and eluted with the buffer at 0.3 M gave 1.26 μmoles of the labeled conjugate (5, n=6) as determined by absorbance measurement at 450 nm, which was a yield of 53%.

II. Antibody binding reactions

Antibody was raised in rabbits against the immunogen 8-(3-carboxypropyl)-1,3-dimethylxanthine-BSA as described by Cook et al, *Res. Comm. in Chem. Pathol. Pharm.* 13:497 (1976).

Antibody binding reactions were conducted at room temperature in 0.1 M sodium phosphate buffer (pH 7.0) and measurements of glucose oxidase activity were carried out in the same buffer at 20° C.

The reagents used in the assay were as follows:

| Reagent | Composition |
| --- | --- |
| A | 0.1 M sodium phosphate buffer (pH 7.0) |
| B | 565 nM theophylline-FAD labeled conjugate or 160 nM $N^6$-(6-aminohexyl) FAD (the FAD derivative) |
| C | antiserum to theophylline (diluted 10 fold in Reagent A) |
| D | apoglucose oxidase (50 nM FAD binding sites per ml) |
| E | monitoring reagent: 200 μg peroxidase/ml; 0.71 mM 4-aminoantipyrine; 71. mM 3,5-dichloro-2-hydroxybenzene sulfonate; 353 mM glucose; and 35 mg BSA/ml. |

Reagents A, B, and C were combined in separate reaction cuvettes in the proportions indicated in Table 2 below. Reagent D (100 μl) and Reagent E (283 μl) were then rapidly and successively added to each reaction mixture followed by incubation for 30 minutes at 20° C. The absorbance at 520 nm was then measured for each cuvette. The results shown in Table 2 are the averages of duplicate runs.

TABLE 2

| Reaction Number | Reagent A (μl) (buffer) | Reagent B (μl) (FAD derivative) | Reagent B (μl) (labeled conjugate) | Reagent C (μl) (antiserum) | Absorbance (520 nm) |
| --- | --- | --- | --- | --- | --- |
| 1 | 617 | — | — | — | 0.046 |
| 2 | 517 | 100 | — | — | 0.584 |
| 3 | 507 | 100 | — | 10 | 0.644 |
| 4 | 477 | 100 | — | 40 | 0.631 |
| 5 | 357 | 100 | — | 160 | 0.629 |
| 6 | 497 | — | 20 | — | 0.690 |
| 7 | 587 | — | 20 | 10 | 0.314 |
| 8 | 577 | — | 20 | 20 | 0.216 |
| 9 | 532 | — | 20 | 40 | 0.224 |
| 10 | 517 | — | 20 | 80 | 0.22 |
| 11 | 437 | — | 20 | 160 | 0.21 |

The results of reactions 2–5 show that the antiserum did not influence the activity of the FAD derivative (i.e., not coupled to theophylline). Reactions 6–11 demonstrated that increasing levels of theophylline antiserum decreased the activity of the labeled conjugate relative to its ability to combine with the apoenzyme.

III. Competitive binding assays

These reactions were carried out as outlined in Part II above except that designated levels of theophylline were combined with Reagents A and B before addition thereto of Reagent C and also that for Reagent C a 100-fold dilution of antiserum was used. The results are shown in Table 3 below.

Reactions 1–3 were controls showing that antibody to theophylline decreases the ability of the labeled conjugate to combine with apoenzyme. Reactions 4–9 demonstrate that FAD activity increases in proportion to the theophylline level in the reaction mixture.

TABLE 3

| Reaction Number | Reagent A (μl) (buffer) | Reagent B (μl) (labeled conjugate) | Theophylline volume added (μl) | Theophylline concentration (μM) | Reagent C (μl) (antiserum) | Absorbance (520 nm) |
| --- | --- | --- | --- | --- | --- | --- |
| 1 | 617 | — | — | — | — | 0.047 |
| 2 | 597 | 20 | — | — | — | 0.932 |
| 3 | 497 | 20 | — | — | 100 | 0.364 |
| 4 | 397 | 20 | 100 | 10 | 100 | 0.703 |
| 5 | 447 | 20 | 50 | 10 | 100 | 0.649 |
| 6 | 397 | 20 | 100 | 1.0 | 100 | 0.507 |

TABLE 3-continued

| Reaction Number | Reagent A (μl) (buffer) | Reagent B (μl) (labeled conjugate) | Theophylline volume added (μl) | Theophylline concentration (μM) | Reagent C (μl) (antiserum) | Absorbance (520 nm) |
|---|---|---|---|---|---|---|
| 7 | 447 | 20 | 50 | 1.0 | 100 | 0.481 |
| 8 | 397 | 20 | 100 | 0.1 | 100 | 0.418 |
| 9 | 447 | 20 | 50 | 0.1 | 100 | 0.377 |

EXAMPLE 4

Homogeneous Binding Assay for Human IgG

I. Preparation of the labeled conjugate-IgG-FAD

To 4.24 mg flavin $N^6$-(6-aminohexyl)-adenine dinucleotide, prepared as described in Example 1 above, was added 2.5 mg dimethyladipimidate dihydrochloride (Pierce Chemical Co., Rockford, Ill.) in 1 ml of water and 5 μl of triethylamine. The reaction was stirred at room temperature for 10 minutes and 40 mg human immunoglobulin (IgG) in 1 ml of 0.1 M sodium pyrophosphate buffer (pH 8.5) was then added. After further stirring at room temperature for 3 hours, the reaction mixture was applied to a 2.5×50 cm G-25 Sephadex (Pharmacia Fine Chemicals, Uppsala, Sweden) column equilibrated and eluted with 0.1 M sodium phosphate buffer (pH 7.0). Fractions from the first eluting peak having absorbance at 450 nm were collected and dialyzed successively against 4 L of 0.1 M sodium phosphate buffer (pH 7.0) for 16 hours, 4 L of 0.1 M sodium phosphate buffer (pH 7.0) containing 1 M sodium chloride for 24 hours, and 0.01 M sodium phosphate buffer (pH 7.0) for 48 hours. Sodium azide was then added to 0.1% (w:v). The reaction material was filtered through a 0.22μ Millipore filter and stored.

II. Antibody binding reactions

The reagents used in the assay were as follows:

| Reagent | Composition |
|---|---|
| A | 0.1 M sodium phosphate buffer (pH 7.0) |
| B | 10 mM 4-aminoantipyrine |
| C | 1.0 M glucose |
| D | 25 mM 3,5-dichloro-4-hydroxybenzene sulfonate in Reagent A |
| E | 1.2 mg/ml horseradish peroxidase in reagent A |
| F | 30% (w:v) bovine serum albumin (Research Products Division, Miles Laboratories, Inc., Elkhart, Indiana) |
| G | IgG-FAD labeled conjugate in solution stored from above |
| H | apoglucose oxidase |
| J | rabbit antiserum against human IgG (obtained from Behring Diagnostics, Somerville, New Jersey) |
| K | standards - human IgG in Reagent A at predetermined levels |
| Reagent mixes were prepared as follows: | |
| Mix #1 - 180 | μl Reagent A, 20 μl Reagent B, 100 μl Reagent D and 5 μl Reagent G (5.4 μM) |
| Mix #2 - 0.3 | ml total volume of various proportions containing the volume of Reagent J indicated in TABLE 4 below with the remaining volume being made up of Reagent A |
| Mix #3 - 80 | μl Reagent D, 50 μl Reagent E, 33 μl Reagent F, 137 μl Reagent A and 1.6 μl Reagent H (4.2 μM FAD-binding sites) |

To 300 μl of Mix #1 was added 300 μl of Mix #2 and 300 μl of Reagent A in separate reaction cuvettes. After at least 10 minutes incubation at room temperature, 300 μl of Mix #3 was added to each reaction. After further incubation for 30 minutes at 20° C., the absorbance at 520 nm was measured in each cuvette. The results were as follows:

TABLE 4

| Volume of antiserum added to prepare Mix #2 | Absorbance (520 nm) |
|---|---|
| 0 | 0.859 |
| 2 | 0.750 |
| 4 | 0.602 |
| 6 | 0.494 |
| 8 | 0.443 |
| 10 | 0.415 |
| 12 | 0.408 |
| 14 | 0.392 |
| 16 | 0.375 |

The results demonstrate that as antiserum level increases, the glucose oxidase activity generated by the FAD label conjugated to IgG decreases.

III. Competitive binding assays

These reactions were carried out using the reagents described in Part II above. The standard solutions (300 μl Reagent K) were combined with Mix #1 in separate reaction cuvettes. Then a mixture of 12 μl of Reagent J and 288 μl of Reagent A was added to each reaction. After 10 minutes 300 μl of Mix #3 was added and the reaction mixtures incubated at 20° C. for 30 minutes. At the end of this period, the absorbance at 520 nm was measured in each cuvette. The results were as follows:

TABLE 5

| Amounts of Human IgG Added (μg) | Absorbance (520 nm) |
|---|---|
| 0 | 0.579 |
| 4 | 0.653 |
| 8 | 0.751 |
| 12 | 0.844 |
| 16 | 0.986 |
| 24 | 1.06 |

The results demonstrate that the glucose oxidase activity generated is directly related to the amount of IgG present in the sample.

EXAMPLE 5

Homogeneous Binding Assay for Phenytoin

I. Preparation of the labeled conjugate-phenytoin-FAD

Figure 3:
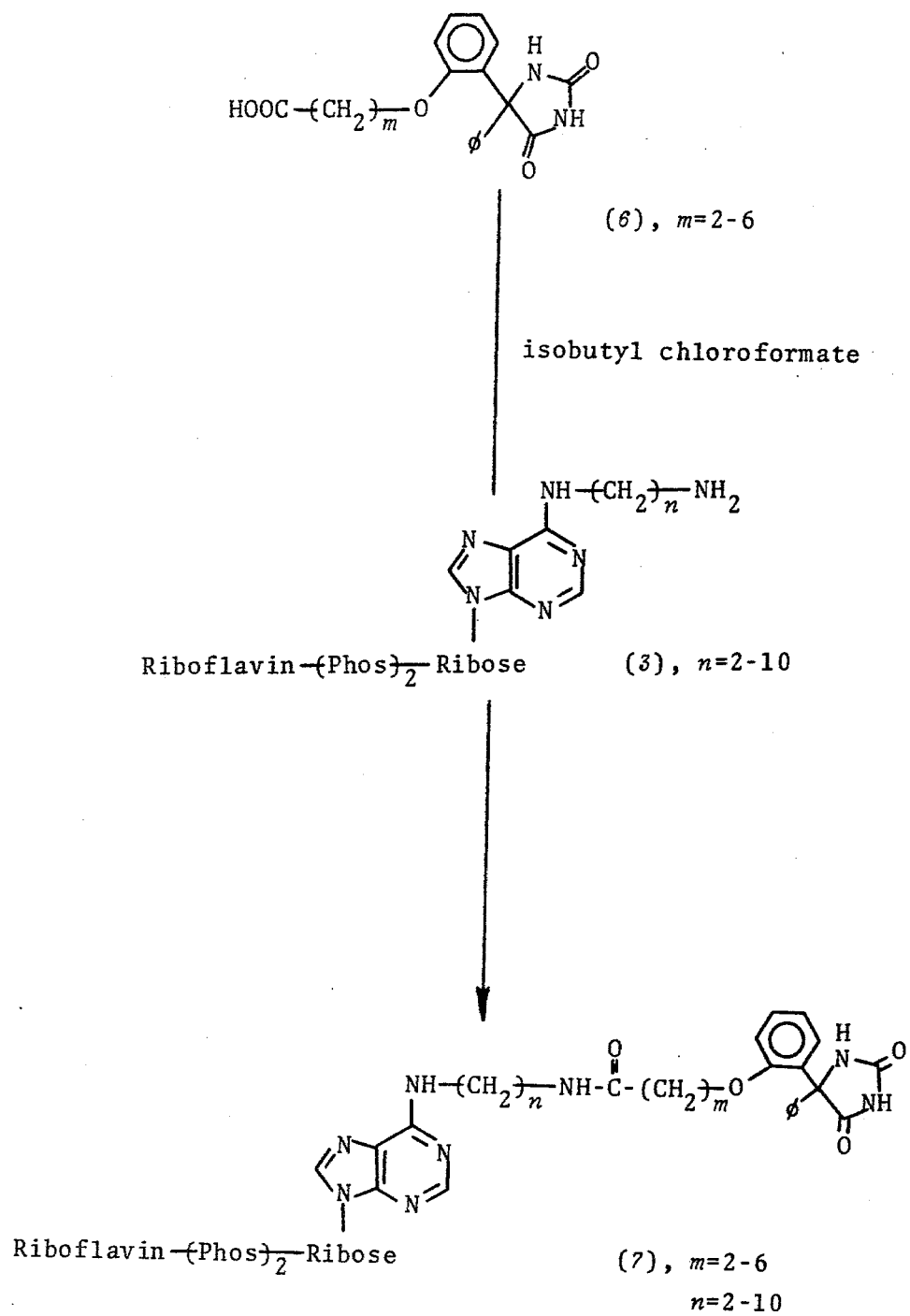

The general reaction sequence for preparing phenytoin-FAD conjugates according to the present invention is shown in FIG. 3 of the drawings. This sequence is exemplified below wherein m=4 and n=6.

To 14.7 mg (40.0 μmol) of 5-(2'-carboxybutyloxyphenyl)-5-phenylhydantoin (described in U.S. Pat. No. 4,182,856 incorporated herein by reference) in 1.8 ml of dry DMF, under argon gas, was added 0.10 ml (40 μmol) of a 400 μM solution of isobutyl chloroformate in DMF. The reaction was stirred one hour at room temperature, and then a solution of 10.0 μmol of flavin $N^6$-(6-aminohexyl)-adenine dinucleotide (3, n=6), prepared as described in Example 1 above, in 2.0 ml of dry dimethylsulfoxide was added followed by 0.05 ml of a 400 μM solution of triethylamine in DMF. The reaction was stirred 19 hours at room temperature, then was diluted to 450 ml with water and was applied to a 1.5×30 cm column of Whatman DE-52 cellulose anion exchange resin (bicarbonate form) with the aid of a peristaltic pump. The column was then eluted with a gradient of 1.5 L of water to 1.5 L of 0.3 M triethylammonium bicarbonate. Fractions of approximately 16 ml were collected. Fractions 70–88 were determined to contain the product (7, m=4, n=6) on the basis of activity with apoglucose oxidase. These fractions were combined and the solution adjusted to pH 7. The yield was determined to be 4.78 μmol (47.8%) on the basis of the absorbance of the solution at 450 nm using the millimolar extinction coefficient of FAD ($\epsilon_{450}=11.3$).

The above-described synthesis of the phenytoin-FAD conjugate (7, m=4, n=6) can be modified to yield labeled conjugates wherein m=2–6 and n=2–10 by replacing the starting material flavin $N^6$-(6-aminohexyl)-adenine dinucleotide with the appropriate flavin $N^6$-(ω-aminoalkyl)-adenine dinucleotide from Example 1, and by replacing the starting material 5-(2'-carboxybutyloxyphenyl)-5-phenylhydantoin with the appropriate 5-(2'-carboxyalkyloxyphenyl)-5-phenylhydantoin as described in U.S. Pat. No. 4,182,856.

II. Binding reactions

The reagents used in the assay were as follows:

| Reagent | Composition |
| --- | --- |
| A | 4 μM FAD binding sites of apoglucose oxidase; 4 mM aminoantipyrine; 0.1 M phosphate, pH 7.0; 0.1% (w:v) bovine serum albumin; 0.02% (w:v) sodium azide |
| B | 3.0 nM phenytoin-FAD conjugate; 0.1 M phosphate, pH 7.0; 2.1 mM sodium 3,5-dichloro-2-hydroxybenzene sulfonate; 0.1 M glucose; 60 μg/ml peroxidase; 1% (w:v) bovine serum albumin; 0.02% (w:v) sodium azide |
| C | antiserum to phenytoin diluted 10 fold with 0.1 M phosphate, pH 7.0 |
| D | serum containing 30 μg/ml phenytoin diluted 50 fold with 0.1 M phosphate, pH 7.0 |

The assay was performed by placing 100 μl of Reagent A and the amounts indicated in Table 6 below of Reagents C and D in disposable plastic cuvettes without mixing and initiating reaction by addition of 1.9 ml of Reagent B. The cuvettes were incubated for 10 minutes at 25° C. in a water bath and the absorbance read at 520 nm. The results are given in Table 6 below. The absorbance due to residual glucose oxidase activity in Reagent A was found to be 0.130 which was substrated from the measured absorbances in the assay to give the absorbance data given in Table 6.

TABLE 6

| Reaction Number | Reagent C (μl; antiserum) | Reagent D (μl; phenytoin) | Absorbance (520 nm) |
| --- | --- | --- | --- |
| 1 | — | — | 0.728 |
| 2 | 10 | — | 0.267 |
| 3 | 10 | 50 | 0.464 |
| 4 | 20 | — | 0.128 |
| 5 | 20 | 50 | 0.323 |
| 6 | 30 | — | 0.098 |
| 7 | 30 | 50 | 0.250 |
| 8 | 40 | — | 0.087 |
| 9 | 40 | 50 | 0.198 |

The results obtained with reactions 1, 2, 4, 6 and 8 show that increasing levels of antiserum to phenytoin progressively decrease the activity of the labeled conjugate phenytoin-FAD with apoglucose oxidase. The results obtained with reactions 3, 5, 7 and 9 show that the activity of the phenytoin-FAD conjugate in the presence of a given level of antiserum is increased by including phenytoin in the competitive binding reaction.

EXAMPLE 6

Homogeneous Binding Assay for Phenobarbital

I. Preparation of the labeled conjugate-phenobarbital-FAD

Figure 4:
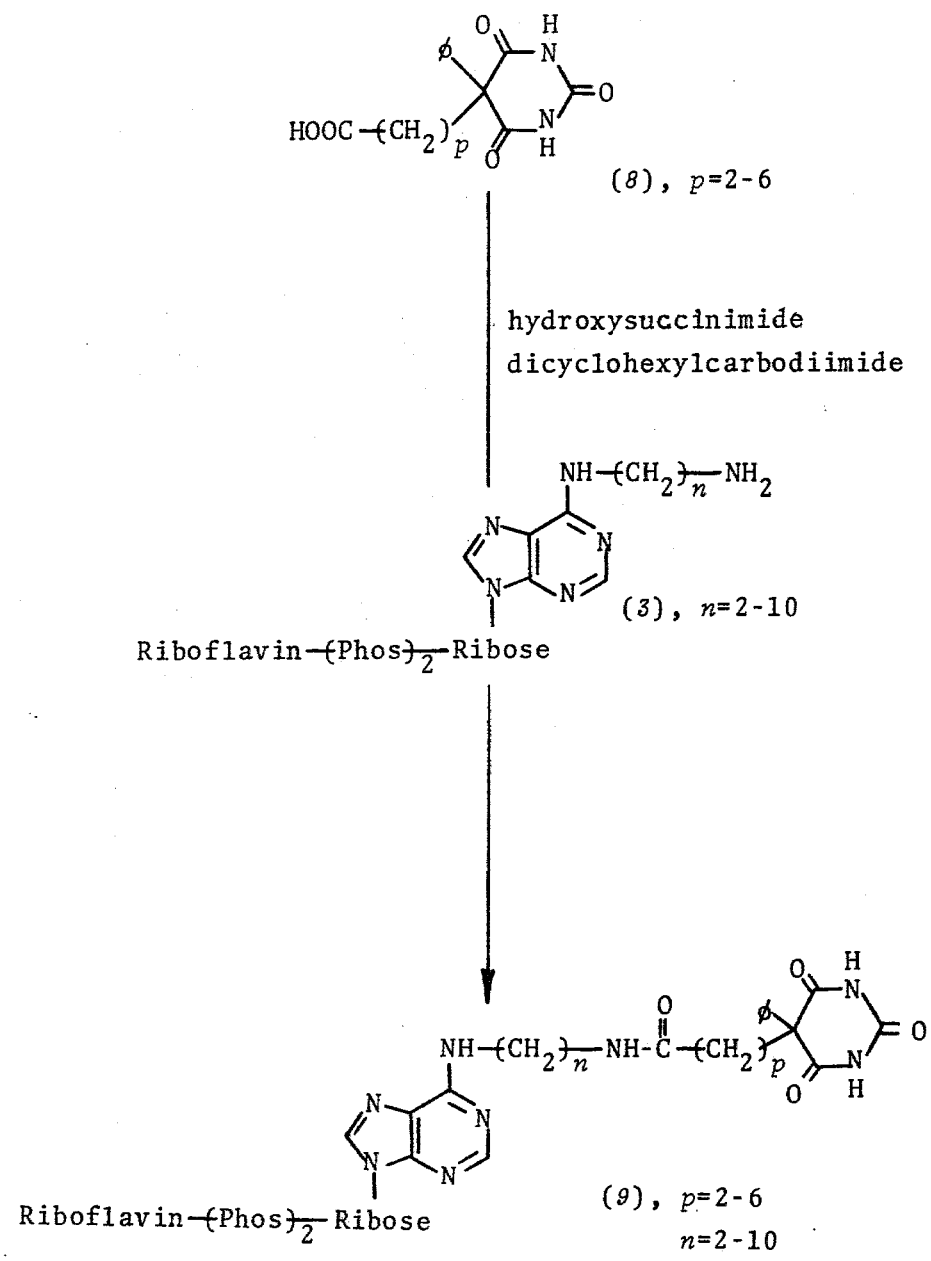

The general reaction sequence for preparing phenobarbital-FAD conjugates according to the present invention is shown in FIG. 4 of the drawings. This sequence is exemplified below wherein p=4 and n=6.

To a mixture of 15 mg (50 μmol) of 5-(4-carboxybutyl)-5-phenylbarbituric acid (8, p=4) [prepared as described by Cook et al, *Quantitative Analytic Studies in Epilepsy*, ed. Kellaway and Petersen, Raven Press (New York 1976), pp. 39–58] and 6.3 mg (55 μmol) of hydroxysuccininimide in 0.5 ml DMF under an argon atmosphere at 0° C. was added a solution of 10.8 mg (52 μmol) dicyclohexylcarbodiimide in 0.5 ml of DMF. The mixture was stirred 30 minutes at 0° C. and then 1 hour at room temperature, and was then added to a 1 ml aqueous solution containing 10 μmol flavin $N^6$-(6-aminohexyl)-adenine dinucleotide (3, n=6), prepared as described in Example 1 above, under an argon atmosphere. An additional 500 μl each of water and DMF were added and the mixture stirred overnight.

The reaction mixture was diluted to 450 ml with water and applied to a 1.5×30 cm column of Whatman DE-52 cellulose anion exchange resin (bicarbonate form) with the aid of a peristaltic pump. The column was then eluted with a gradient of 1.5 L of water and 1.5 L of 0.2 M triethylammonium bicarbonate. Fractions of approximately 14 ml were collected, with fractions 105–150 determined to contain the product (9, p=4, n=6) on the basis of activity with apoglucose oxidase. These fractions were combined and the solution adjusted to pH 7. The yield was determined to be 3.95 μmol (40%) on the basis of the absorbance of the solution at 450 nm using the millimolar extinction coefficient of FAD ($\epsilon_{450}=11.3$).

The above-described synthesis of the phenobarbital-FAD conjugate (9, p=4, n=6) can be modified to yield labeled conjugates wherein p=2–6 and n=2–10 by replacing the starting material flavin $N^6$-(6-aminohexyl)-adenine dinucleotide with the appropriate flavin $N^6$-(ω-aminoalkyl)-adenine dinucleotide from Example 1, and by replacing the starting material methyl 5- bromovalerate in the procedure of Cook et al, supra, with the appropriate methyl ω-bromoalkanoate.

II. Binding reactions

The reagents used in the assay were as follows:

| Reagent | Composition |
|---|---|
| A | same as in Example 5 |
| B | same as in Example 5 except the labeled conjugate was phenobarbital-FAD at approximately 3 nM |
| C | antiserum to phenobarbital diluted 10 fold with 0.1 M phosphate, pH 7.0 |
| D | serum containing 60 μg/ml phenobarbital diluted 10 fold with 0.1 M phosphate, pH 7.0 |

The assay protocol was the same as that described in Example 5 except that the incubation period was 15 minutes. For this assay the correction factor for residual glucose oxidase activity was found to be 0.155. The results, with corrected absorbance readings, are given in Table 7 below.

TABLE 7

| Reaction Number | Reagent C (μl; antiserum) | Reagent D (μl; phenobarbital) | Absorbance (520 nm) |
|---|---|---|---|
| 1 | — | — | 1.240 |
| 2 | 10 | — | 0.306 |
| 3 | 10 | 10 | 0.820 |
| 4 | 20 | — | 0.293 |
| 5 | 20 | 10 | 0.717 |
| 6 | 30 | — | 0.271 |
| 7 | 30 | 10 | 0.586 |
| 8 | 40 | — | 0.278 |
| 9 | 40 | 10 | 0.522 |

The results obtained with reactions 1, 2, 4, 6 and 8 show that increasing levels of antiserum to phenobarbital progressively decreases the activity of the phenobarbital-FAD conjugate with apoglucose oxidase. In competitive binding reactions 3, 5, 7 and 9, the presence of phenobarbital increased the activity of the phenobarbital-FAD conjugate at given antiserum levels.

What is claimed is:

1. A flavin adenine dinucleotide derivative of the formula:

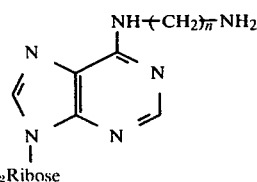

wherein Riboflavin-(-Phos-)₂Ribose represents the riboflavin-pyrophosphate-ribose residue in flavin adenine dinucleotide and n is an integer from 2 through 10.

2. The derivative of claim 1 wherein n=6.

3. A flavin adenine dinucleotide-labeled theophylline conjugate of the formula:

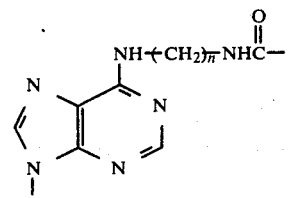

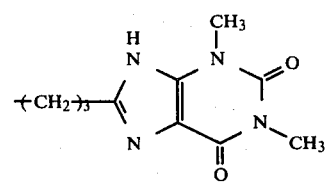

wherein Riboflavin-(-Phos-)₂Ribose represents the riboflavin-pyrophosphate-ribose residue in flavin adenine dinucleotide and n is an integer from 2 through 10.

4. The conjugate of claim 3 wherein n=6.

5. A flavin adenine dinucleotide-labeled phenytoin conjugate of the formula:

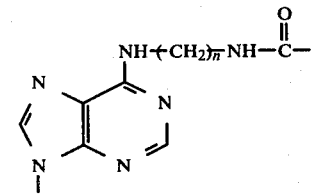

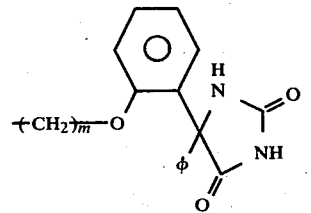

wherein Riboflavin-(-Phos-)₂Ribose represents the riboflavin-pyrophosphate-ribose residue in flavin adenine dinucleotide, φ is phenyl, n is an integer from 2 through 10, and m is an integer from 2 through 6.

6. The conjugate of claim 5 wherein n=6.

7. The conjugate of claim 6 wherein m=4.

8. A flavin adenine dinucleotide-labeled phenobarbital conjugate of the formula:

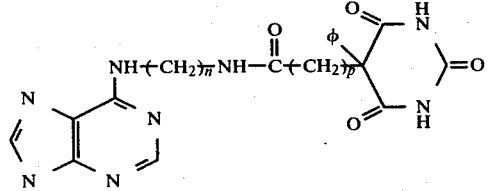

wherein Riboflavin-(-Phos-)₂Ribose represents the riboflavin-pyrophosphate-ribose residue in flavin adenine dinucleotide, φ is phenyl, n is an integer from 2 through 10, and p is an integer from 2 through 6.

9. The conjugate of claim 8 wherein n=6.

10. The conjugate of claim 9 wherein p=4.

* * * * *